(12) United States Patent
Shahidi

(10) Patent No.: US 6,850,794 B2
(45) Date of Patent: Feb. 1, 2005

(54) ENDOSCOPIC TARGETING METHOD AND SYSTEM

(75) Inventor: Ramin Shahidi, San Francisco, CA (US)

(73) Assignee: The Trustees of the Leland Stanford Junior University, Palo Alto, CA (US)

( * ) Notice: Subject to any disclaimer, the term of this patent is extended or adjusted under 35 U.S.C. 154(b) by 184 days.

(21) Appl. No.: 09/957,477

(22) Filed: Sep. 20, 2001

(65) Prior Publication Data

US 2002/0077544 A1 Jun. 20, 2002

Related U.S. Application Data

(60) Provisional application No. 60/234,963, filed on Sep. 23, 2000.

(51) Int. Cl.[7] ................................................. A61B 5/05
(52) U.S. Cl. ..................................................... 600/427
(58) Field of Search ................................ 600/102, 109, 600/117, 118, 300, 407–472; 606/130; 73/1.01, 1.75, 1.79, 1.81; 348/130; 128/922, 898, 916; 356/51, 125, 143, 138, 908, 909

(56) References Cited

U.S. PATENT DOCUMENTS 6,517,478 B2 * 2/2003 Khadem ...................... 600/117

* cited by examiner

*Primary Examiner*—Ali Imam
(74) *Attorney, Agent, or Firm*—Lee & Hayes, PLLC

(57) ABSTRACT

The invention provides a system for enhancing the ability of a surgeon to access a target site within a patient. The system includes a data file containing volumetric scan data of a region of the patient that includes the target site, a display device, and a movable imagining tool for producing on the display device, an image of visible patient structure seen by the tool. A computer in the system operates to (i) determine the position and/or orientation of the tool in the frame of reference of the patient, (ii) identify the scan-data coordinates (either x,y or x,y,z coordinates) of the target site, and (iii) project on the video image on the display device, indicia that indicate the lateral position of the target site with respect to the patient structure imaged on the display device.

12 Claims, 4 Drawing Sheets

ENDOSCOPIC TARGETING METHOD AND SYSTEM

This patent application claims priority to U.S. Provisional Patent Application Ser. No. 60/234,963 filed on Sep. 23, 2000, which is incorporated in its entirety herein by reference.

FIELD OF THE INVENTION

This invention relates to image-guided surgery, and in particular, to an endoscopic targeting method and system.

BACKGROUND OF THE INVENTION

Endoscopic surgical tools are used in a variety of surgical procedures. Typically, such tools include an optical system for visualizing patient structure at or near a target site, and a surgical tool for carrying out desired operations at the site, e.g., removal of tissue for biopsy, surgical removal of necrotic or tumorous tissue, surgical repair of tissue structure, etc. U.S. Pat. Nos. 5,928,137, 5,968,061, 5,681, 262, 5,840,017, 5,840,014 and 5,830,126 describe representative types of endoscopic surgical tools. In an endoscope-guided operation, the surgeon will need to know in which direction, and what distance to advance the tool in order to optimally access the target site. Since an endoscopic tool can only view surface structure, the surgeon will often have difficulty in locating and/or accessing a target site, which is likely to be hidden from endoscopic view.

It would therefore be desirable to provide an endoscopic targeting method and system to assist a surgeon in performing an endoscopic surgical procedure or endoscopic examination of a patient.

SUMMARY OF THE INVENTION

The invention includes, in one aspect, a system for enhancing the ability of a surgeon to access a target site within a patient. The system includes a data file containing volumetric scan data of a region of the patient that includes the target site, a display device, a movable imagining tool for producing on the display device, an image of visible patient structure seen by the tool, where the position of the tool is tracked relative to the position of the patient, and a computer operatively connected to data file, display screen, and tracking device.

The computer operates to (i) determine the position and/or orientation of the tool in the frame of reference of the patient, (ii) identify the scan-data coordinates (either x,y or x,y,z coordinates) of the target site, and (iii) project on the video image on the display device, indicia that indicate the lateral position of the target site with respect to the patient structure imaged on the display device.

In one embodiment, in which the indicia give 2-D information about the target site, the projected indicia define an area on the image that borders the lateral position of the target site. The area is to defined by a function related to the depth of the depth of the target site below the patient structure imaged on the display device, such as an error function related to the degree of uncertainty in patient target site in the imaged structure.

The computer may further function to determine whether the target site is located within the lateral field of the displayed patient-structure image, and if it is not, to project on the displayed image, indicia indicating the lateral direction of the target site with respect to the imaged patient structure.

The system may further include a calibration tool operatively connected to the computer for supplying to the computer, information about the imaging tool's field of view, position, orientation and direction.

Where the imaging tool is an endoscopic surgical tool having an interior channel through which a surgical tool can be manipulated, the system may further include structure for tracking the position of said surgical tool relative to the imaging element in the imaging tool, and the computer may further function to project on the video image on the display device, indicia that provide information about the position of the target site in relation to the end of the surgical tool.

In another aspect, the invention includes a method for enhancing the ability of a surgeon to access a target site within a patient. The method includes the steps of storing in a data file, volumetric scan data of a region of the patient, including a target site within the patient region, moving an imaging tool for producing on a display device, an image of visible patient structure seen by the tool, and tracking the position of the tool relative to the position of the patient. The method employs a computer screen, for (i) determining the position and/or orientation of the tool in the frame of reference of the patient, (ii) identifying the scan-data coordinates (either x,y or x,y,z coordinates) of the target site, and (iv) projecting on the video image on the display device, indicia that indicate the lateral position of the target site with respect to the patient structure imaged on the display device.

Various above-mentioned embodiments applicable to the system of the invention are also applicable to the method.

These and other objects and features of the invention will be more fully appreciated when the following detailed description of the invention is read in conjunction with the accompanying drawings.

DETAILED DESCRIPTION OF THE INVENTION

Figure 1:
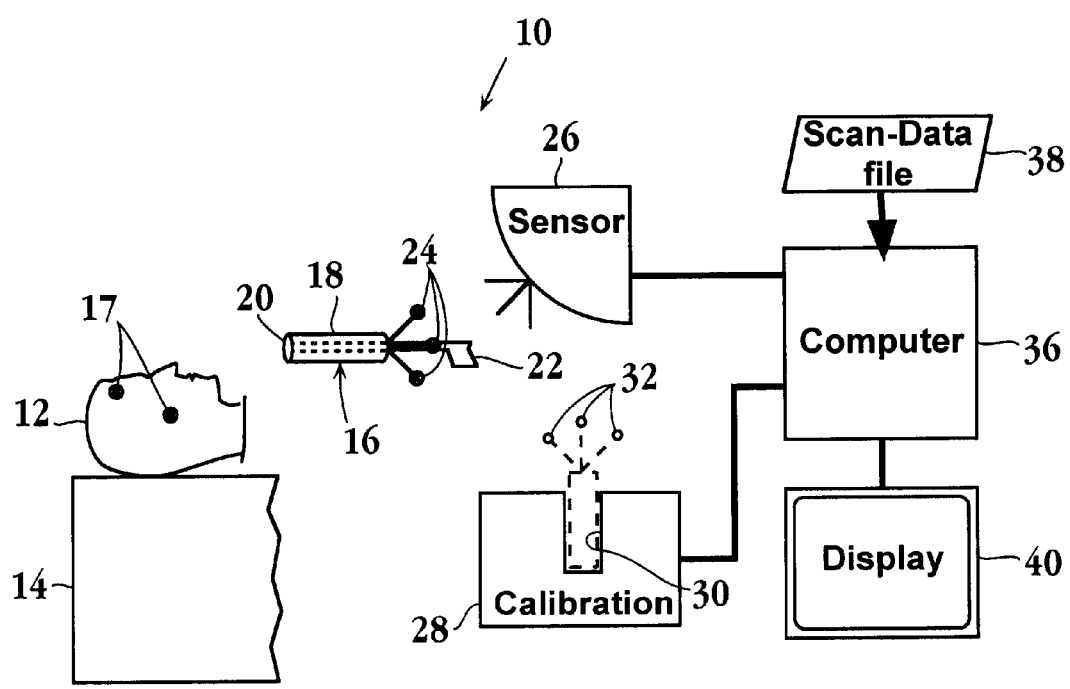
FIG. 1 illustrates components of the system of the invention, shown in a surgical setting.

FIG. 1 illustrates components of a system 10 of the invention, shown in operative relationship to the head region of a patient 12 supported on a surgical table 14. For purposes of illustrating the describing the invention, the patient region of interest—the surgical target region—is within the a region of the patient's body head accessible by an endoscopic tool inserted through the throat or nostrils, e.g., a region of the brain near a sinus cavity. It will be appreciated that the invention is applicable to any body region, e.g., body joints, where surgery with an imaging tool, e.g., an endoscope, is carried out. For use in tracking patient position during surgery, a plurality of tracking elements, such as LEDs 17, are attached at fixed positions on the patient surface.

The system includes an endoscopic surgical tool 16, or other surgical imaging tool, such as a microscope ocular, or simple endoscope. Tool 16 includes an elongate tool body 18 which terminates at its distal end in an endoscopic lens 20, and which provides an interior channel through which a surgical appliance 22 may be moved. Exemplary endoscopic tools are those described in U.S. Pat. Nos. 5,928,137, 5,968,061, 5,681,262, 5,840,017, 5,840,014 and 5,830,126. In addition, tool 16 includes a plurality of tracking elements, such as LED's 24, used in tracking the position, direction and orientation of the tool.

In the embodiment of the system shown, a sensing unit is part of a position tracking system, which is preferably an optical tracking system (hereafter "OTS") having sensing unit or sensor 26 mounted overhead in view of the operating table scene, and tracking elements, e.g., LEDs attached to the patient and endoscopic tool as noted above. The LED's attached to the movable objects are preferably designed to emit streams of pulsed infrared signals which are sensed by a plurality of infrared detectors (not shown) contained in the sensing unit. The sensing unit and movable objects are connected to the computer, which controls the timing and synchronization of the pulse emissions by the LED's and the recording and processing of the infrared signals received by the detectors.

The OTS further includes software for processing these signals to generate data indicating the position and orientation (direction and twist) of the movable objects in the frame of reference of surgical station. The OTS may generate the position data on a real-time basis, so that as the endoscopic tool is moved, for example, or the patient moves, their positions in a common coordinate system, e.g., the patient's coordinate system, are known. One preferred OTS is described in PCT application WO 9900052 A1 for Image Generation of Three Dimensional Object, which is incorporated herein by reference.

A variety of alternative tracking devices and methods for tracking the position of a movable tool with respect to a patient, such as those detailed in U.S. Pat. Nos. 5,198,877, 5,987,349, and 5,622,170 are also available.

A calibration tool 28 in the system is used in calibrating the image seen by the endoscope lens with a known endoscope field of view, instrument position (e.g., x,y,z coordinates of a point in the endoscope lens) and orientation, which includes both instrument direction (the angle of the tool with respect to a fixed position) and angular orientation or twist (the angular position of the tool about its long axis). To this end, tool 28 has an elongate cavity 30 which receives the lens-end of the endoscopic instrument, and a multi-point pattern (not shown) at the lower end of the barrel which is imaged by the instrument in its calibration position. The calibration tool is also equipped with tracking elements, such as LEDs 32, used by the OTS to determine the position of the calibration tool.

With the endoscopic instrument placed in the calibration tool, the pattern image seen by the instrument is recorded, as is (i) the position and orientation of the calibration tool, and (ii) the position and orientation of the endoscopic instrument in the calibration tool. This endoscope calibration information is used, in part, in registering the patient-surface image seen by the endoscope lens with the patient-structure coordinates of the pre-operative scan data. The calibration tool is described in U.S. patent application Ser. No. 60/193,209, filed Mar. 30, 2000 for "Device for Calibrating a Medical Instrument, Including Determining Field-of-View and compensation for Lens Distortion and Offset", which application is hereby incorporated by reference.

System 10 includes a data-scan file 38 which stores pre-op scan data, typically obtained at a scanning station. The scan-data consists of voxel coordinates, corresponding scan-data, e.g., density values, for each voxel, and coordinates for registration features, e.g., LEDs 17 or other fiducials, which are present on the patient during scanning, and are maintained in place during the subsequent surgical operation. The scan data file is operatively connected to computer 36, which carries out the data processing operations of the system, to be described. Also connected to the computer are sensor 26 and a display device 40, such as a conventional color monitor screen.

As will be described in greater detail below, the computer is operatively connected to data file, display screen, and tracking device, for (i) determining the position and/or orientation of the instrument in a patient coordinate system, (ii) identifying the scan-data coordinates of the target site in the patient coordinate system, and (iii) projecting on the video image on the display device, indicia that indicate the lateral position of the target site with respect to the patient structure imaged on the display device.

Figure 2:
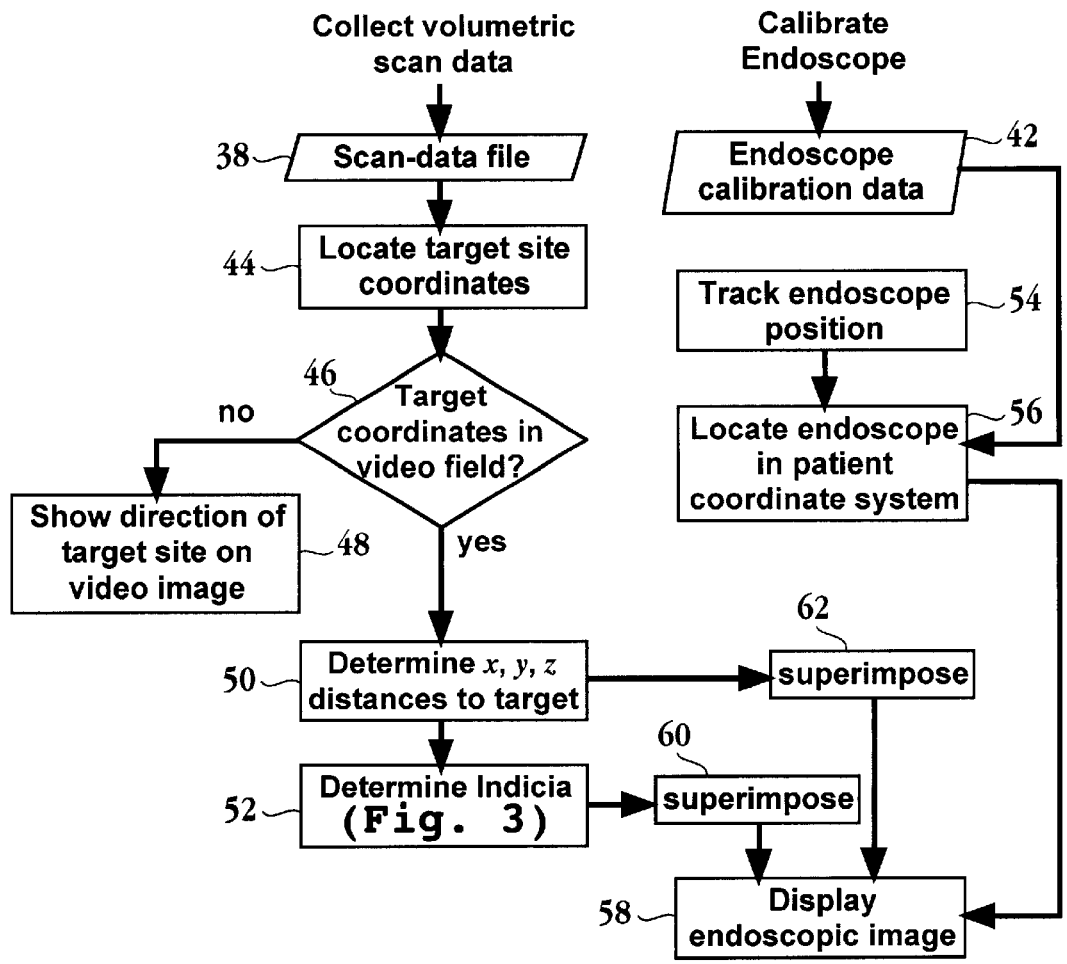
FIG. 2 is a flow diagram of the operation of the system of the invention.

Looking now at FIG. 2, volumetric scan data of the patient region of interest is stored in scan-data file 38. Also prior to the surgical procedure, the endoscopic tool is calibrated, as above, and information relating to the pattern image seen by the endoscope in relation to endoscope position, direction, and orientation is stored in an endoscope calibration data file 42. By tracking the position, orientation, and direction of the instrument in space, as at 54, and tracking the position of the instrument with reference and knowing the position of the patient in space (both determined from the OTS), the position, direction, and orientation of the instrument can be placed in the patient frame of reference, i.e., coordinate system, as at 56. Alternatively, the position of the instrument can be tracked directly in the patient frame of reference to provide the same information. At the same time, knowing the endoscope field of view, the view seen by the endoscope within the body can be matched with the stored CT data, which is also in the frame of reference of the patient. This matching is effective to superimpose the endoscopic image on a surface image of patient structure which would be reconstructed from the patient CT data. The endoscopic image is displayed conventionally on display device 40, as shown at 58.

Prior to the surgery or during surgery, the surgeon has identified the target site of interest, and the coordinates of this site in the scan data are specified, e.g., by clicking on target structure revealed in a perspective view of the target region reconstructed from the CT data. The target-site coordinates specified are stored as at 44.

Figure 4:
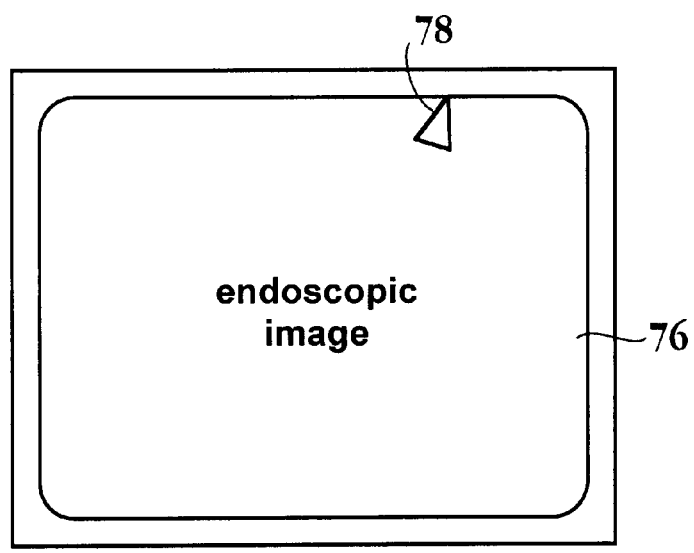
FIG. 4 shows a video image display where the target site is out of the field of the image.

For purposes of explanation, it is convenient to consider the patient coordinate system in terms of a z axis extending between a selected point on the endoscopic tool, e.g., a point at the center of the lens, and a target site point. The x,y plane is then a plane normal to this axis and containing (having x,y coordinates in common with) the video image seen by the endoscopic tool. The x,y distances within the video image are known from the previously-input field of view of the lens. If the x,y coordinates of the target site are outside of the image, as tested at 46, the computer will construct an indicium, e.g., arrow, that is placed at the periphery of the video image to indicate the x,y direction of the target site in relation to the image on the display screen. This feature is illustrated in FIG. 4, which is intended to represent a display screen showing a video image 76 of patient structure and an arrow 78 indicating that the target site is "off" the screen in the direction of the arrow. This allows the surgeon to move toward the target site by moving in the direction of the arrow.

If the target site x,y coordinates are within the video image x,y coordinates, the system then determines the distance along the z axis between the instrument and target site, namely $(x^2+y^2+z^2)^{1/2}$, and may display this distance to the user at the display screen, as at 60. The system also determines indicia which will be placed on the video image to indicate to the user the following types of information (i) the x,y (lateral) position of the target site, (ii) the z distance from the instrument to the target site, and optionally, (iii) the uncertainty in target-site position.

Figure 3:
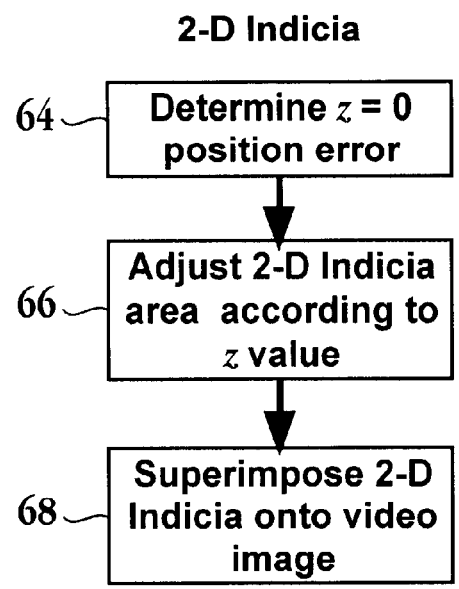
FIG. 3 is a flow diagram of the system operation in generating 2-D and 3-D indicia.

To illustrate, and with reference to FIG. 3, the system-operation steps at the left in the figure operates first to calculate a target-site position error, as at 64. This error represents the uncertainty in determined target-site position due to uncertainty in patient position, instrument position, and uncertainty about the target site within the patient. This error is a function of distance, since the degree of position uncertainty increases with distance from the target site, and may thought of as a conical function emanating from a small error "circle" at the target and expanding on moving away from the target site, in this case, along the z axis. The conical slices along the z axis then define an area (circle) whose size (diameter) is related to the error function. This calculation is made at 66 in the figure.

The indicia which define the area in the 2-D display are positioned so that the center of the area, e.g., circle, has the x,y coordinates of the target site. The size of the defined area is then adjusted, as at 66, to correspond (by same scaling factor) relate to the z-axis distance to the target. The thus-determined indicia are then displayed on the video image, as at 68.

Figure 5A:
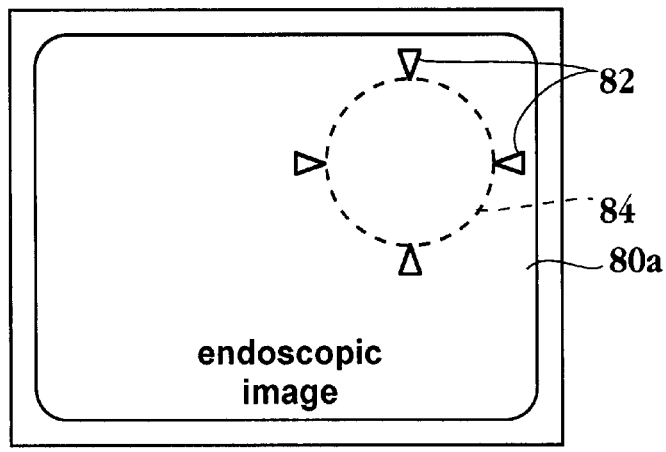
FIGS. 5A–5C illustrate various states of 2-D indicia projected on an endoscopic image to assist a surgeon in accessing a target site in an endoscopic surgical procedure.
Figure 5B:
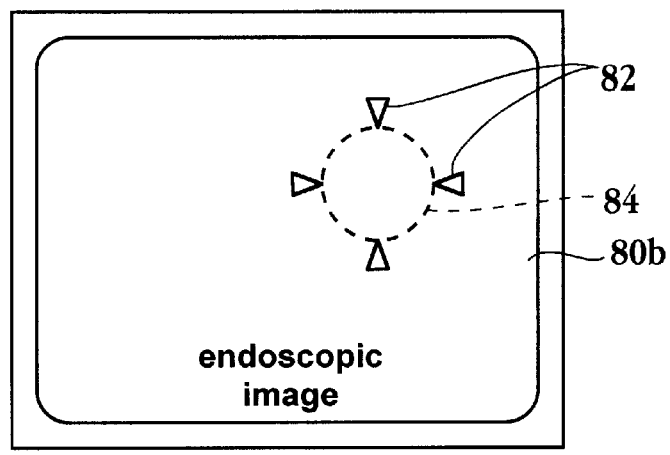
Figure 5C:
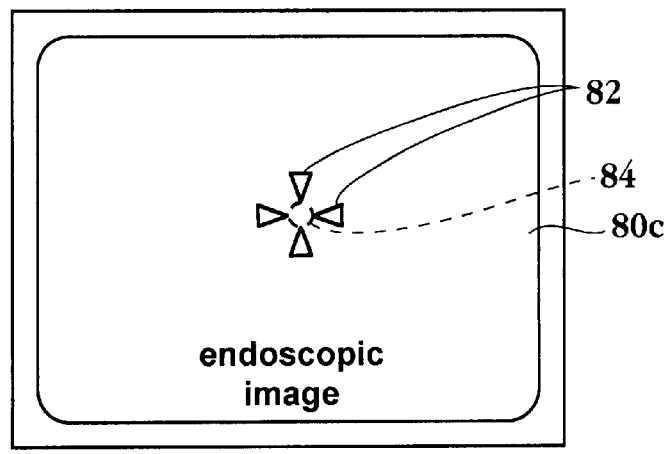

FIGS. 5A–5C show three hypothetical endoscopic video image 80a, 80b, 80c having 2-D indicia placed on the image in accordance with the invention. The indicia in this example are four arrows, such as arrows 82, that define a circular area (within the dotted line 84). The x,y coordinates of the indicia (the center of the circle) correspond to the x,y coordinates of the target site and the diameter of the circle, to the z-axis distance between the instrument and target site.

The three figures show the change in indicia as the instrument is moved from a position down and to the left of the target site (FIG. 5A) progressively closer in x,y,z coordinates to the target site. (FIGS. 5B and 5C). When the instrument is moved to the target site (FIG. 5B), the arrows should be at the center of the screen, with the diameter of the circle then representing the uncertainty in target-site position.

The method and system have been described above with reference to tracking the "view" point of the endoscopic image (the lens elements) toward a target site. It will be appreciated that the same principles and operations can be adapted to tracking the surgical tip of the instrument toward the target site. In this case, a second tracking structure which tracks the z-axis movement of the instrument tip with respect to the endoscope lens is used by the computer to determine the position of the tip along the z axis. The indicia displayed on the video image are adjusted accordingly to show the shorter distance between the tip and target site.

Alternatively, one set of indicia, e.g., indicia of one color, may be used to indicate the position of the instrument lens element from the target, and a second set of indicia having, for example, another color would indicate the distance of the instrument tip from the target site. The two sets of indicia would allow the surgeon to move the entire instrument, and the surgical tip of the instrument independently to advance the tip toward the target site in an efficient manner.

In another related embodiment, the system uses the scan data to generate a subsurface image, preferably a perspective subsurface image of the target region, as described, for example, in above noted PCT application WO 9900052 A1 for Image Generation of Three Dimensional Object. The reconstructed image is displayed to the user on a display screen, e.g., alongside the endoscopic image. In accordance with the present invention, the target-site indicia determined as above are then superimposed on the reconstructed image, employing the coordinates to the image to place and scale the indicia. In this embodiment, the surgeon may visualize target position and distance in both endoscopic and virtual images reconstructed from the scan data.

Although the system and method of the invention have been described with reference to particular embodiments and implementations, it will be appreciated that a variety of changes and modifications can be made without departing from the claimed invention. In particular, a variety of 2-D and 3-D indicia and indicia formats can be constructed to assist the surgeon in accessing the target site.

What is claimed is:

1. A system for enhancing the ability of a surgeon to access a target site within a patient, comprising
   a data file containing volumetric scan data of a region of the patient that includes the target site,
   a display device,
   a movable imagining tool for producing on the display device, an image of visible structure seen by the tool, where the position and/or orientation of the tool is tracked with respect to the patient coordinate system, and
   a computer operatively connected to data file and display screen for (i) determining the position and/or orientation of the tool in a patient coordinate system, (ii) identifying the scan-data coordinates of the target site in the patient coordinate system, and (iii) projecting on the video image on the display device, indicia that indicate (a) the direction of the target site, if the target site is outside the patient structure imaged on the display device, and (b) the lateral position of the target site with respect to the patient structure imaged on the display device and the distance between the tool and the target site, if the target site is within the patient structure imaged on the display device.

2. The system of claim 1, wherein the system includes a tracking device for tracking the position and direction of the instrument with respect to patient position.

3. The system of claim 2, wherein said indicia define an area whose center corresponds to the lateral position of the target site, and whose size is related to the distance between the instrument and the target site.

4. The system of claim 3, wherein the size of the area defined by the indicia is calculated by an error function representing the degree uncertainty in patient target site in the imaged structure.

5. The system of claim 1, wherein said computer is operatively connected to a calibration device for receiving information therefrom with respect to the imaging tool's field of view, position, direction orientation.

6. The system of claim 1, wherein (i) said imaging tool is an endoscope having an interior channel through which a surgical tool can be manipulated, (ii) the system further includes structure for tracking the position of said surgical tool relative to said imaging device, and (iii) the computer operates to project on the video image on the display device, indicia relating the position of the target site in relation to the tip of said tool.

7. A method for enhancing the ability of a surgeon to access a target site within a patient, comprising
- storing in a data file, volumetric scan data of a region of the patient, including a target site within the patient region,
- moving an imagining tool for producing on a display device, an image of visible patient structure seen by the tool,
- tracking the position of the tool relative to the position of the patient, and
- by means of a computer a computer operatively connected to data file and display screen, (i) determining the position and/or orientation of the tool in the frame of reference of the patient, (ii) identifying the scan-data coordinates of the target site, and (iii) projecting on the video image on the display device, indicia that indicate the (a) the direction of the target site, if the target site is outside the patient structure imaged on the display device, and (b) the lateral position of the target site with respect to the patient structure imaged on the display device and the distance between the tool and the target site, if the target site is within the patient structure imaged on the display device.

8. The method of claim 7, wherein said tracking is done by a tracking device for tracking the position and direction of the instrument with respect to patient position.

9. The method of claim 7, wherein said wherein said projecting includes projecting on the video image on the display device, indicia that define an area whose center corresponds to the lateral position of the target site, and whose size is related to the distance between the instrument and the target site.

10. The method of claim 9, wherein the size of the area defined by the indicia is calculated by an error function representing the degree of uncertainty in patient target site in the imaged structure.

11. The method of claim 7, wherein said determining includes calibrating the imaging tool with respect to field of view, position, direction and orientation.

12. The method of claim 7, wherein the imaging tool that is moved is an endoscope having an interior channel through which a surgical tool can be manipulated, and said projecting includes projecting on the video image on the display device, indicia relating the position of the target site in relation to the tip of said tool.

* * * * *